United States Patent
Fedorov et al.

[11] Patent Number: 6,129,760
[45] Date of Patent: Oct. 10, 2000

[54] ARTIFICIAL LENS

[76] Inventors: Svyatoslav Nikolaevich Fedorov, Dostoevskogo,d.1/21,kv.32, Moscow, Russian Federation, 103030; Andrei Valentinovich Zolotorevsky, Sokolnichesky val,d.10,k.2,kv.156, Moscow, Russian Federation, 103113; Sergei Nikolaevich Bagrov, Startovaya,9,k.2,kv.236, Moscow, Russian Federation, 129336; Sergei Viktorovich Novikov, Fersmana,d.3,k.1,kv.19, Moscow, Russian Federation, 117312

[21] Appl. No.: 09/285,771
[22] Filed: Apr. 5, 1999
[30] Foreign Application Priority Data Apr. 10, 1998 [RU] Russian Federation ............ 98106887

[51] Int. Cl.$^7$ ....................................................... A61F 2/16
[52] U.S. Cl. .............................................................. 623/6.43
[58] Field of Search ................................. 623/6.49, 6.45, 623/6.44, 6.43, 6.4, 6.38, 6.11

[56] References Cited

U.S. PATENT DOCUMENTS

| 4,840,627 | 6/1989 | Blumenthal | 623/6.44 |
| 5,047,051 | 9/1991 | Cumming | 623/6.45 |
| 5,192,319 | 3/1993 | Worst | 623/6.43 |
| 5,476,514 | 12/1995 | Cumming | 623/6.45 |

FOREIGN PATENT DOCUMENTS 2097006  11/1997  Russian Federation .

*Primary Examiner*—David H. Willse
*Assistant Examiner*—Suzette J. Jackson
*Attorney, Agent, or Firm*—Jacobson, Price, Holman & Stern, PLLC

[57] ABSTRACT

An artificial lens (AL) for an implantation during an extraction of cataract of any etiology as well as for an implantation into the aphakic eye comprising an optic portion means and supporting elements means wherein in order to exclude displacement of the optic portion and he supporting elements as affected by any capsular forces, the supporting elements are provided with at least one groove in the form of ellipse arc in the section plane perpendicular to the AL optic axis.

7 Claims, 2 Drawing Sheets

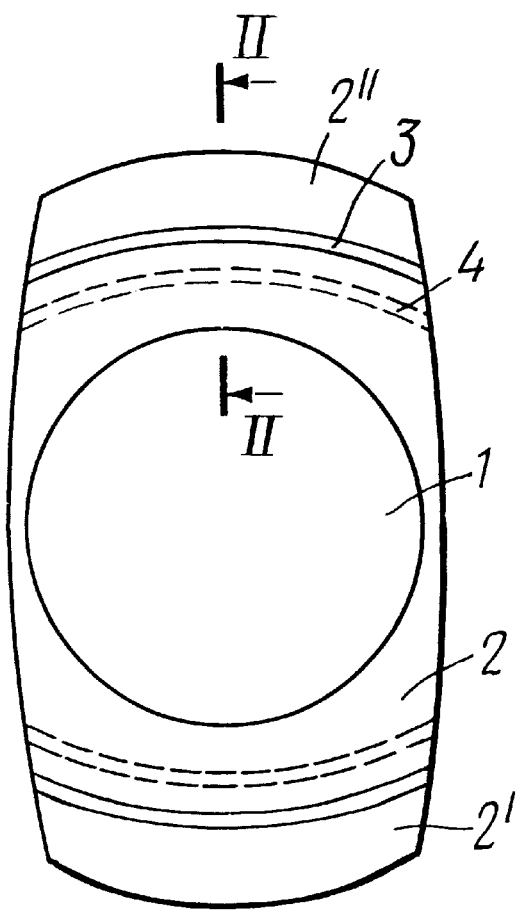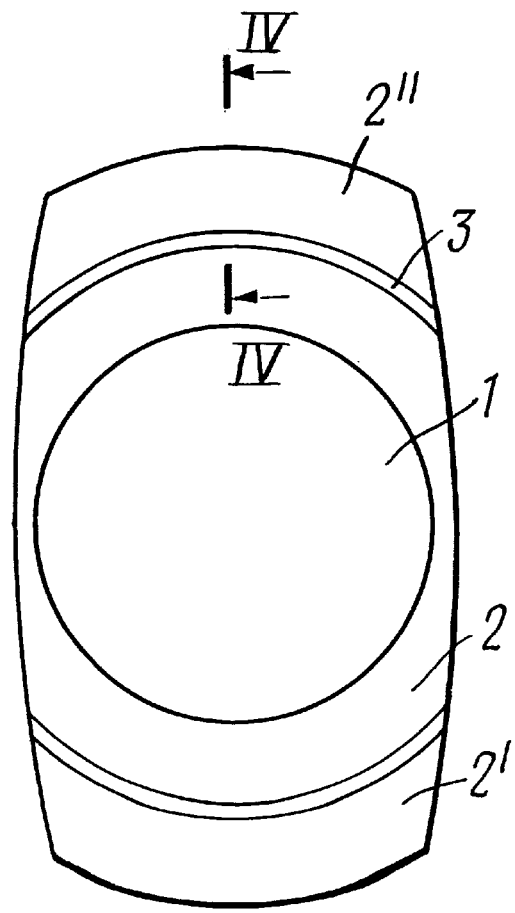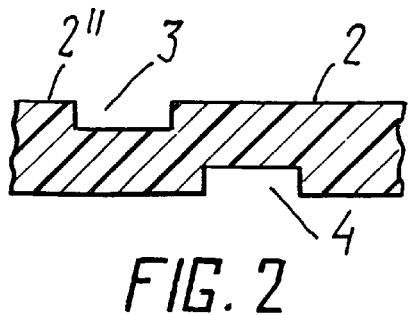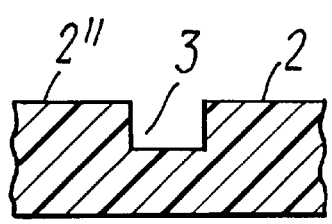

ARTIFICIAL LENS

FIELD OF INVENTION

The invention relates to medicine, more particularly to ophthalmology, and can be useful for intraocular correction of aphakia.

BACKGROUND OF THE INVENTION

Use of intraocular lenses or artificial lenses is widely known for correcting impairment of vision. They are mainly designed to correct aphakia following cataract extraction.

As a rule, these lenses comprise an optic body and supporting elements, shape, dimensions and configuration of which depend on physical characteristics of the material.

Often following implantation of the known lenses, there arises the problem associated with a possibility of an uncontrollable displacement of the optic portion that results in impairment of ocular refraction, iridal dispigmentation and as a sequence, in the development of secondary pigmental glaucoma.

Furthermore, mechanic injury of the surrounding tissues induced by displaced optic portion, results in impairment of their trophism, washing out of proteins and their deposition on the optic portion of artificial lens (AL) that means loss of its optic characteristics.

Various attempts were earlier Undertaken to reduce post operative complications through preventing uncontrollable displacement of the optic portion following its implantation caused by the action of capsular forces occuring because of discrepancy between the dimensions of the AL optic portion and the capsule due to outgrowth of lens masses in case of their incomplete extraction during surgery. Therefore, when sufficiently large displacement occurs in a part of patients, there are observed iridal injury and dispigmentation resulting in the development of secondary glaucoma.

Earlier, the authors of this invention had developed the AL (RF patent No.2097006 granted to Fedorov et al.) manufactured from elastic biologically inert material and comprising optic portion and diametrically disposed support elements in the form of truncated disc, distal portions of supporting elements being manufactured centrally concave and their frontal surfaces having grooves disposed at right angle to vertical axis.

Said grooves provide on supporting elements, permitted to exclude negative effect of those portion of capsular forces that are directed at right angle to said grooves.

However, it was found that this AL was efficient only in those cases when capsular forces caused by contraction of ligaments of Zinn were directed strictly perpendicular to the grooves. Taking into consideration the fact that capsular forces can act in any directions, then in these cases, this results in uncontrollable displacement of the optic portion due to bending of support elements as affected by such forces as well as in uncontrollable displacement of one or both haptic elements.

There is known the U.S. Pat. No. 5,476,514 comprising optic body and haptic on which grooves parallel to vertical lens axis, are provided and presence of such grooves in this AL is directed at accomplishing controllable displacement of optic portion as affected by capsular forces that promotes accomodation of the eye following surgery.

Accordingly, need exists in providing AL for implantation following extraction of cataract of any etiology as well as for implantation into the aphakic eye.

BRIEF DESCRIPTION OF THE INVENTION

An object of the invention is to provide AL that would permit to exclude post operative complications associated with displacement of the optic part as affected by any capsular forces connected with implantation of AL.

Another object of the invention is to provide AL with such manufacturing supporting elements that would exclude possibility of their displacement as affected by capsular forces.

Still another object of the invention is to provide AL implantation of which would not depend on individual dimensions of the capsular sac of patient.

The above objects as well as the other objects of the invention are achieved by that in the artificial lens manufactured from elastic biologically inert material and comprising an optical body means and a supporting portion means comprising at least two supporting elements, said supporting elements are provided with at least one groove in the form of ellipse arc in the section plane perpendicular to the AL optic axis.

Preferably, the supporting portion means is provided in the form of truncated disc.

The above grooves can be provided on both front and back surface of the supporting elements or on both sides at the same time their depth being from 10 $\mu$m to 500 $\mu$m, the width being within the range from 10 $\mu$m to 1 mm and the length from 10 $\mu$m to 10 mm.

It is reasonable that at least one of the supporting elements is additionally provided with at least one stiffening rib that permits to additionally strengthen the construction in those particular cases of the eye pathology following surgery when it is needed.

Preferably, cross section of the groove is rectangle, taper, triangle or ellipse.

AL with such disposition and dimensions or the grooves and with use of stiffening ribs, does not permit optic port to uncontrollably displace in the lens capsule or vice versa, in case of need, allows one to perform predetermined displacements that in its turn, reduces probability of image distortion as well as occurence or secondary cataract and pigmental glaucoma.

BRIEF DESCRIPTION OF DRAWINGS

The above objects as well as the other objects of the invention, will be disclosed below during description of detailed but not limiting embodiment of this invention and by the accompanying drawings, in which:

FIG. 1 is a frontal view of the claimed AL according to the invention;

FIG. 2 is section II—II on FIG. 1;

FIG. 3 is one of the embodiments of the proposed AL;

FIG. 4 is section IV—IV on FIG. 3;

DESCRIPTION OF THE PREFERRED EMBODIMENT

Let us refer to FIG. 1 where there is shown the proposed AL comprising a lens 1 and a supporting portion 2 in the form of truncated disc consisting of at least two opposite supporting elements 2' and 2" with two grooves 3 and 4 in the form of ellipse arcs on each of the opposite supporting elements from front and back sides of the AL.

The supporting elements can be manufactured from any biologically inert material.

The term "biologically inert material" as used herein, refers to materials selection of which is easy for those skilled in the art of ophthalmology and first of all, depends on their elasticity. Such materials include silicons, hydrogel materials etc. Generally speaking, selection of such materials should be guided by the list of materials approved by FDA for use in ophthalmology.

Shapes and dimensions of the grooves as well as of the stiffening ribs in case of their presense, are determined by particular object, i.e. strengthening or weakening AL construction that in its turn, is determined by an area of the supporting elements.

Depth of the grooves that is not less than 10 μm, imparts hinge mobility to the given site of support element but it can not be more than 500 μm since in this case, a significant weakening of AL construction occurs down to its destruction under the effect of capsular forces.

Groove width can not be more than 1 mm since this would result in loss of strength and uncontrollable displacements of the optic part in the eye of patient.

Cross section of the grooves can be rectangle, taper, triangle or ellipse.

FIG. 2 shows the section of the ellipse arc grooves along line II—II on FIG. 1 in the form of rectangle.

FIG. 3 shows one of the AL embodiments according to the invention that consists of a lens 1, a supporting portion 2 in the form of truncated disc comprising at least two supporting elements 2' and 2" and having only one groove 3 in the form of circle arc on each of the opposite supporting elements.

FIG. 4 shows a groove section along line IV—IV in the form of rectangle.

The groove section in the form of taper, triangle and ellipse, is not shown on the drawings.

Figure 5:
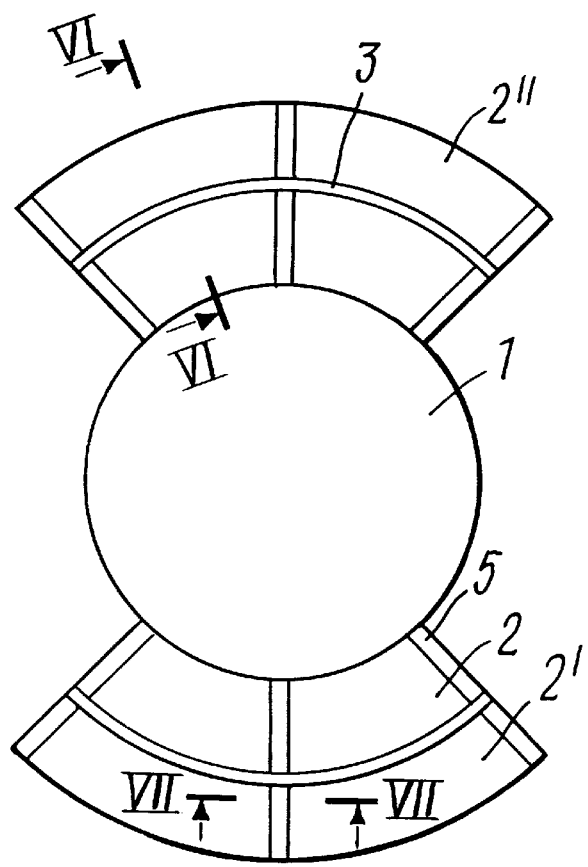
FIG. 5 is one of the embodiments of the proposed AL.
Figure 6:
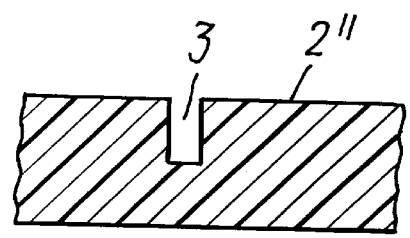
FIG. 6 is section VI—VI on FIG. 5.
Figure 7:
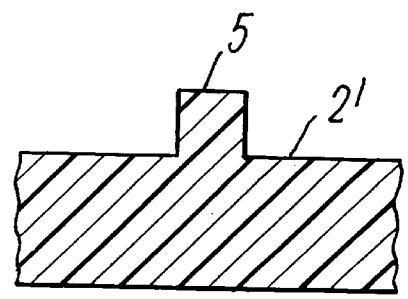
FIG. 7 is section VII—VII on FIG. 5.

FIG. 5 demonstrates one of the AL embodiments consisting of a lens 1, a supporting portion 2 in the form of truncated disc comprising at least two opposite supporting elements 2' and 2" and having a groove 3 in the form of circle arc with a section along line VI—VI in the form of rectangle (FIG. 6) on each of the opposite supporting elements. In this embodiment, AL is provided with three stiffening ribs 5 on each of the opposite supporting elements (stiffening rib is shown in a section along line VII—VII on FIG. 5).

Construction strengthening by providing stiffening ribs is used in particular when there is a risk of dorsal capsule fibrosis development during post operative period. And construction weakening by providing stiffening ribs, is used in particular in cases of appeared outgrowth probability of lens masses.

Methods of manufacturing the AL, are widely disclosed in literature and do not require special knowledge and attraction of those skilled in different arts.

The proposed lens can be manufactured for example by form of polymerisation, formation, grinding etc.

In any case, manufacture of the AL is not difficult for those skilled in the art.

Order of implanting the proposed AL

A cataractal incision is done, an extracapsular cataract extraction is performed, the lens is grasped with pincers by one portion of the supporting element and the other portion of the supporting element is brought behind the other portion of the supporting element into a capsular sac, then using a hook for inserting the supporting element, first portion of the supporting element is brought into an upper arch of the cansular sac, and the cataractal incision is sutured.

Particular examples of using the proposed AL

EXAMPLE 1

Female patient K.Vision acuity OD-0,01 non correctable. OS-0,3,intraocular pressure (IOP) OD—19 mm Hg (2,53 kPa, mature cataract of the right eye. Extracapsular cataract extraction was performed with implantation of artificial lens according to the invention, with two grooves in the form of ellipse arcs having width 10 μm, depth 30 μm and length 7 mm.

Three months post operation: OD—0,7 without correction. Lens occupies correct position, IOP=18 mm Hg (2,4 kPa).

EXAMPLE 2

Patient P.Vision acuity OS-0,04 non correctable. OD-1,0, IOP OS—17 mm Hg (2,72 kPa), mature cataract of the left eye. Extracapsular cataract extraction was performed with implantation of artificial lens according to the invention, with one groove in the form of circular arc having width 50 μm, depth 50 μm and length 8 mm.

Three months post operation: OS—0,8 without correction. Lens occupies correct position, IOP=18 mm HP (2,4 kPa).

EXAMPLE 3

Patient Zh. Vision acuity OD-0,06 non correctable. OS-0,9, intraocular pressure (IOP)OD—19 mm Hg (2,53 kPa), mature cataract of the right eye. Extracapsular cataract extraction was performed with implantation of artificial lens according to the invention, with one groove in the form of circular arc having width 50 μm, depth 100 μm and length 8 mm and tree stiffening ribs on each of support elements.

Three months post operation: OD—0,9 without correction. Lens occupies correct position, IOP=18 mm Hg (2,4 kPa).

For clarity, description of the invention embodiments under consideration is done using particular specific terminology. However, the invention is not limited by the terms that are accepted herein and it should be appreciated that every such term covers all the equivalent terms that are used to settle the same objects.

While this invention is disclosed in association with the preferred embodiment, it will be understood that various modifications and versions may occur to those skilled in the art, e.g. the quantity of stiffening ribs can vary. Such modifications and versions not departing from the spirit and scope of the present invention as defined by the claims that follow.

What is claimed is:

1. An artificial lens (AL) manufactured from elastic biologically inert material comprising an optic part means and supporting portion means comprising at least two supporting elements provided with at least one groove wherein said groove is provided in the form of ellipse arc in the section plane perpendicular to the AL optic axis, said supporting elements having a depth within a range from 10 μm to 500 μm, a width within a range from 10 μm to 1 mm and a length within a range from 10 μm to 10 mm.

2. The AL in accordance with claim 1 wherein said supporting portion is provided in the form of a truncated disc.

3. The AL in accordance with claim 1 wherein said supporting portion has two grooves.

4. The AL in accordance with claim 3 wherein said grooves can be provided on front and back surface of said supporting elements or on both sides simultaneously.

5. The Al in accordance with claim 1, wherein at least one of said at least two supporting elements is additionally provided with at least one stiffening rib.

6. The AL in accordance with claim 1 wherein a cross section of the groove is rectangle, taper, triangle or ellipse.

7. An artificial lens (AL) manufactured from elastic biologically inert material comprising an optic part means and supporting portion means comprising at least two supporting elements provided with at least one groove wherein said groove is provided in the form of ellipse arc in the section plane perpendicular to the AL optic axis, at least one of said at least two supporting elements being additionally provided with at least one stiffening rib.

* * * * *